United States Patent [19]

Newell

[11] 4,220,166

[45] Sep. 2, 1980

[54] METHOD OF RESTORING NORMAL MOISTURE LEVEL TO HAIR WITH SEVERE MOISTURE DEFICIENCY

[75] Inventor: Gerald P. Newell, Hanover Park, Ill.

[73] Assignee: Helene Curtis Industries, Inc., Chicago, Ill.

[21] Appl. No.: 912,359

[22] Filed: Jun. 5, 1978

[51] Int. Cl.$^2$ .......................... A45D 7/04; A61K 7/06
[52] U.S. Cl. ......................................... 132/7; 424/70; 424/71
[58] Field of Search ................. 132/7, 9; 424/70, 71, 424/65, DIG. 2, 362, 365

[56] References Cited

U.S. PATENT DOCUMENTS

| 3,235,457 | 2/1966 | Loder | 424/70 X |
| 3,450,674 | 6/1969 | Walles | 424/71 |
| 3,683,939 | 8/1972 | Johnsen | 424/70 |
| 3,822,312 | 7/1974 | Sato et al. | 424/70 |
| 3,948,943 | 4/1976 | Eberhardt et al. | 424/65 |
| 4,047,537 | 9/1977 | Shaw | 132/7 |
| 4,076,800 | 2/1978 | Marsh et al. | 424/70 |
| 4,115,549 | 9/1978 | Scott | 132/7 X |

FOREIGN PATENT DOCUMENTS

| 44-22440 | 9/1969 | Japan . | |
| 49-27643 | 7/1974 | Japan | 424/70 |
| 51-20639 | 6/1976 | Japan | 424/70 |
| 7604794 | 11/1976 | Netherlands | 424/70 |

OTHER PUBLICATIONS

Cosmetics Science and Technology-Editor: Edward Sagarin, Interscience Publishers, Inc., New York 1957, pp. 382-383, 405.
American Perfumer and Cosmetics, vol. 78, No. 10, Oct. 1963, "Proteins in Cosmetics," pp. 69-72.
Drug & Cosmetic Industry, 84(H), p. 440-(1960)-Thomsen.

*Primary Examiner*—Stuart S. Levy
*Attorney, Agent, or Firm*—Dressler, Goldsmith, Shore, Sutker & Milnamow, Ltd.

[57] ABSTRACT

A method of restoring the normal moisture level to hair initially having a severe moisture deficiency comprising the steps of: (1) shampooing the hair with a moisture stabilizing shampoo; (2) at least once a week, applying a moisture gain intensive conditioner to freshly shampooed hair; (3) at least once a week, applying a moisture gain deep heat treatment to said freshly shampooed hair; (4) conditioning the shampooed hair with a moisture stabilizing composition when said deep heat treatment or said moisture gain intensive treatment is not used; and (5) thereafter applying a moisture control styling lotion; each of said shampoos, conditioners and lotions comprising from about 0.01 to about 1.0 weight percent of sodium-2-pyrrolidone-5-carboxylate, from about 0.05 to about 5.0 weight percent of glycerin and from about 0.05 to about 5.0 weight percent of glycerin and from about 0.05 to about 5.0 weight percent of protein derived from a collagenous source.

4 Claims, No Drawings

METHOD OF RESTORING NORMAL MOISTURE LEVEL TO HAIR WITH SEVERE MOISTURE DEFICIENCY

BACKGROUND OF THE INVENTION

This invention relates to a method for restoring a normal moisture level in severely moisture deficient hair.

The use of hair coloring or bleaching products, permanents, straighteners, blowdryers and exposure to sun, wind, indoor heating, etc. are all drying and damage the hair by robbing it of moisture. Moisture deficient hair is dull, brittle and lifeless.

A number of products have been developed in recent years to improve the condition of hair. While many of the available hair-conditioning compositions improve the sheen, combability and manageability of hair, they do little to restore and maintain the normal moisture content of hair. Thus there is a need for improved products and methods which can restore and maintain the normal moisture content of initially severely moisture deficient hair as well as condition it to improve its sheen, combability and the like. The present invention provides a method for achieving this result.

Laden U.S. Pat. No. 3,235,457, issued Feb. 15, 1966, discloses the use of the free acid or the hygroscopic salts of 2-pyrrolidone-5-carboxylic acid, 1-methyl-2-pyrrolidone-5-carboxylic acid and 4-methyl-2-pyrrolidone-5-carboxylic acid as humectants in cosmetic compositions which are to be applied to hair or skin. Laden discloses incorporating the humectants into the cosmetics and other compositions to prevent the products from losing moisture and drying out in storage. Laden further teaches that the humectants must be present in an amount of at least 2 weight percent of such compositions, and preferably from 4 to 10 weight percent. Glycerin is also known to be a humectant.

It has now surprisingly been found that when from about 0.01 to about 1 weight percent of sodium-2-pyrrolidone-5-carboxylate is incorporated into hair treatment compositions such as shampoos, conditioners, and the like, along with glycerin and protein derived from a collagenous source, and such compositions are used in concert with each other in a prescribed manner, the moisture level can be restored to severely moisture deficient hair.

Thus the present invention provides a method of restoring the normal moisture content to severely moisture deficient hair.

SUMMARY OF THE INVENTION

The present invention provides a method of restoring the normal moisture level to severely moisture deficient hair comprising the steps of: (1) shampooing the hair with a moisture stabilizing shampoo; (2) at least once a week, applying a moisture gain intensive conditioner for at least 25 minutes to freshly shampooed hair; (3) at least once a week, applying a moisture gain deep heat treatment to said freshly shampooed hair; (4) alternatively conditioning the shampooed hair with a moisture stabilizing composition on days when either the deep heat treatment or the moisture gain intensive treatment are not used; and (5) thereafter applying a moisture control styling lotion; each of said shampoos, conditioners and lotions comprising from about 0.01 to about 1.0 weight percent of sodium-2-pyrrolidone-5-carboxylate, from about 0.05 to about 5.0 weight percent of glycerin and from about 0.05 to about 5.0 weight percent of protein derived from a collagenous source.

The compositions used in the practice of this invention, i.e., shampoos, styling compositions and conditioners each contain from about 0.01 to about 1.0 weight percent of sodium-2-pyrrolidone-5-carboxylate, from about 0.01 to about 5.0 weight percent of glycerin and from about 0.01 to about 5 weight percent of protein derived fron collagenous sources, in addition to the generally used ingredients of such compositions. Hereinafter, the unique combination of the three ingredients will be referred to as the two humectants and protein.

The term "moisture stabilizing shampoo" refers to a shampoo containing the above two humectants and protein.

The term "moisture stabilizing conditioner" refers to a conditioner containing the combination of two humectants and protein which is applied to the hair after shampooing and then immediately rinsed from the hair.

The term "moisture control styling composition" refers to styling compositions which can either be smoothed on prior to the hair being set or if the hair is to be blown dried to blow dry compositions as set forth hereinbelow, both of which contain the two humectants and protein.

The term "moisture gain intensive conditioner" refers to a conditioner containing the two humectants and protein which is applied to the hair for at least 15 minutes after a shampooing and thereafter rinsed from the hair.

The term "moisture stabilizing night supplement gel" refers to a gel containing the two humectants and protein which is applied in small amounts and worked through the hair prior to bedtime, and allowed to stay on throughout the night to additionally moisturize the hair.

The term "moisture gain deep heat conditioner" refers to a conditioner containing the two humectants and protein which is applied to the hair and then heat applied for at least 15 and preferably 30 minutes.

In addition to the unique combination of the sodium-2-pyrrolidone-5-carboxylate, glycerin and protein in the compositions which are used in the practice of this invention, the compositions may additionally comprise quaternary conditioners, detergents, thickeners, fatty esters, non-quaternary conditioning agents, fragrance, fragrance solubilizers and the like as is common in such compositions.

DETAILED DESCRIPTION OF THE PREFERRED EMBODIMENTS

The present invention relates to or provides a method of restoring the normal moisture level to severely moisture deficient hair comprising the steps of: (1) shampooing the hair with a moisture stabilizing shampoo; (2) at least once a week, applying a moisture gain intensive conditioner for at least 25 minutes to freshly shampooed hair; (3) at least once a week, applying a moisture gain deep heat treatment to said freshly shampooed hair; (4) alternatively conditioning the shampooed hair with a moisture stabilizing composition on days when either the deep heat treatment or the said moisture gain intensive treatment are not used; and (5) thereafter applying a moisture control styling lotion; each of said shampoos, conditioners and lotions comprising from about 0.01 to about 1.0 weight percent of sodium-2-pyrrolidone-5-carboxylate, from about 0.05 to about 5.0 weight percent of glycerin and from about 0.05 to about 5.0 weight percent of protein derived from a collagenous source.

In order to determine whether hair is severely moisture deficient, the hair to be tested is dried out in a vacuum oven and accurately weighed. The hair is then allowed to equilibrate at an ambient room humidity and reweighed accurately. The increased weight is due to moisture pickup. The percent moisture regain is then calculated as follows:

$$\frac{\text{Wt. of hair at a given room humidity} - \text{Wt. of dry hair}}{\text{Wt. of dry hair}} \times 100 = \%$$

The average results for normal hair is approximately 6.3. Moderately moisture deficient hair regains an average of 5.6 percent moisture. Severely moisture deficient hair regains an average of 5.0 percent moisture.

Depending upon whether the compositions used in the practice of this invention are formulated as shampoos or as various types of conditioners or setting lotions, the compositions used in the practice of this invention can include other ingredients which are generally usual for the particular type of compositions. Thus, for example, if the composition of this invention is formulated as a shampoo, it can include from about 5 to about 50 weight percent of a suitable detergent such as sodium lauryl sulfate or a sodium lauryl sulfate containing detergent, i.e., Dynol SAM sold by Richardson Co., alone or together with an amphoteric surface active agent such as the mono-sodium salt of N-lauryl-iminodipropionic acid, i.e., Deriphat 160C sold by General Mills, which can be present in the shampoo in an amount of from about 0.05 to 10 weight percent, preferably 0.1 to about 5 weight percent of the shampoo and a non-ionic detergent such as a coconut diethanolamide, i.e., Ninol 2012 sold by Stepan Chemical Company. In addition, the shampoo used in the practice of this invention can include foam boosters and stabilizers such as lauryl dimethylamine oxide, i.e., AMMONYX-LO sold by Onyx Chemicals, which can be present in an amount of from about 1 to 15 weight percent, preferably from about 2 to 10 weight percent of the composition. The shampoos can also include chelating agents such as ethylenediaminetetraacetic acid (EDTA), preservatives such as Methyl Parasept sold by Tenneco Chemical Company, glutaraldehyde monomethyloldimethyl hydantoin and the like. The shampoo formulations can also include perfuming agents, coloring agents and the like.

The conditioning compositions of this invention can include, in addition to the sodium-2-pyrrolidone-5-carboxylate, glycerin and protein, conditioners such as alkylmethyl bis (polyoxyethylene) quaternary ammonium salt, i.e., Ethoquad 0/12 sold by Armak Chemical Company, which can be present in an amount of from about 0.5 to about 5 weight percent, preferably from about 2 to about 4 weight percent; a cationic surface active agent such as cetyltrimethyl ammonium chloride (29% active) sold under the tradename Barquat CT-429 by Lonza, Inc. and also sold by Armak Chemical Company; stearic acid, which can be present in an amount of from about 0.5 to about 3 weight percent, preferably 1.0 to 2.0 weight percent; glycerol monostearate, which can be present in an amount of from about 0.5 to about 3.0 weight percent, preferably from about 1 to about 2 weight percent, cetyl alcohol which can be present in an amount of about 0.5 to about 5 weight percent, preferably from about 2.0 to about 3 weight percent; polyethylene glycol polymer of ethylene oxide having an average molecular weight of 3,000-3,700 such as that sold by Union Carbide Chemical Company under the tradename Carbowax 4000 which can also be present in an amount of 0.5-5.0 weight percent, and pantothenyl alcohol, which can be present in an amount of 0.05 to 5 weight percent of the composition, in addition to perfuming agents, coloring agents and the like.

It will be understood to those skilled in the art that the above ingredients variously serve as conditioning agents, thickeners and opacifiers, anti-static agents and the like. Generally speaking, when the unique combination of humectants and protein are combined with any or all of the above ingredients, the resulting conditioner is referred to herein as a moisture stabilizing conditioner.

If a moisture control setting conditioner is desired, the three principal ingredients can, for example, be combined with denatured ethanol such as SD alcohol 40, generally at about 25 to 35 weight percent of the composition; from about 1 to about 10 weight percent of a film forming resin such as the 80% vinylpyrrolidone-20% dimethylaminoethyl methacrylate copolymer quaternized with diethyl ammonium sulfate such as GAF Quat 734 sold by General Aniline and Film Corporation; from 0.1 to about 2 weight percent of a quaternary anti-static conditioner such as dimethyl difatty ammonium chloride in aqueous isopropanol such as that sold by Ashland Chemical Company under the tradename ADOGEN 432 CG, and a cationic surface active agent such as Ethoquad 0/12, identified above. The moisture control setting conditioner can additionally include perfumes and non-ionic surface active agents which also serve as perfume-solubilizers such as a polyoxyalkylene derivative of sorbitan monolaurate, i.e., TWEEN 20 sold by ICI United States, Inc., and coloring agents.

If the hair is to be blown dry or set with hot curlers, a thermal styling protective lotion is provided by combining the protein and two humectants with from about 0.2 to about 10 weight percent, preferably from about 0.5 to about 5 weight percent of, for example, polyvinylpyrrolidone (PVP 30) sold by GAF Corporation, a quaternary conditioner such as a polymer of hydroxyethylcellulose reacted with epichlorohydrin and quaternized with trimethylamine Polymer JR 400 sold by Union Carbide Corporation and an anti-static conditioner with 5 percent propylene glycol as a stabilizer such as oleyldimethyl benzyl ammonium chloride, sold under the tradename AMMONYX KP, by Onyx Chemicals. The thermal styling lotion can additionally include perfuming agents and the like.

In the practice of this invention, hair having a severe moisture deficiency is further treated with a supplemental gel conditioner, which is applied from one to three times a week or more nightly to further condition and restore the normal moisture content to moisture deficient hair. Such supplemental gel conditioners can contain, in addition to the protein and two humectants, from about 0.1 to about 2.0 weight percent of a water soluble high molecular weight carboxyvinyl polymer, i.e., Carbopol 940 sold by B. F. Goodrich Chemical Company or a similar polymer, from about 20 to about 30 weight percent of denatured ethanol such as 200 proof SD alcohol 40 and a non-ionic surfactant such a polyoxyalkylene derivative of sorbitan monolaurate, the aforementioned TWEEN 20 sold by ICI United States, Inc.

A moisture gain intensive conditioner for damaged hair is also provided by this invention. The intensive conditioner is used weekly on initially severely moisture deficient hair and allowed to remain on the hair for about 25 minutes. In addition to the two humectants and protein, the intensive conditioner can include various hair conditioners such as an aqueous cationic surface active agent such as cetyltrimethyl ammonium chloride, i.e., BARQUAT CT-429 in an amount of from about 0.5 to about 5 weight percent of the compositions sold by Lonza, Inc., from about 0.5 to about 5.0 weight percent of an acid stabilized glycerol monostearate, i.e., Lexemul AR sold by Inolex Corporation, from about 0.5 to about 5.0 weight percent of a high molecular weight cetyl alcohol-polyethylene glycol ether complex, i.e., Promulgen D sold by Robinson-Wagner Co., from about 0.5 to about 10 weight percent of mineral oil, preferably 65 to 75 weight, from about 0.5 to about 10 weight percent of isopropyl myristate, from about 0.5 to about 10 weight percent of a thickener such as cetyl alcohol and from about 0.5 to about 10 weight percent of ethylene glycol monostearate, i.e., Product EG-19 sold by Clintwood Chemical Company.

A moisture conditioner hair spray composition can be formulated by incorporating from about 1 to about 15 percent by weight of a water soluble resin consisting of 60% vinylpyrrolidone-40% vinylacetate copolymer, i.e. PVP/VA-E-635, sold by General Amiline and Film Corporation, and from about 0.05 to about 1.5 percent by weight of a copolymer of dimethyl polysiloxane and a polyoxylalkylene ester such as Silicone Fluid SF-1066 sold by General Electric, and from 40 to 80 weight percent of alcohol, i.e., SD Alcohol 40.

The preferred proteins are water or alcohol soluble polypeptides derived from collagenous sources such as those sold under the tradenames Lexein X250 and WSP-A200 Protein sold by Inolex Corporation.

The following examples illustrate the compositions of this invention.

EXAMPLE 1

MOISTURE STABILIZING SHAMPOO

A moisture stabilizing shampoo composition is formulated using the following ingredients:

| Ingredient | Weight Percent |
| --- | --- |
| Sodium DL-2-pyrrolidone-5-carboxylate (50% aqueous soln.) | 0.10 |
| Glycerin | 0.10 |
| Protein | 0.10 |
| Dynol SAM | 42.00 |
| Ninol 2012 | 1.00 |
| Lauryl dimethylamine oxide | 2.00 |
| Deriphat 160C | 0.10 |
| Water | to 100 percent |

In addition, the above shampoo composition also includes preservatives, chelating agents, coloring agents, perfume and the like. The following example illustrates such a composition.

EXAMPLE 2

MOISTURE STABILIZING SHAMPOO

| Ingredient | Weight Percent |
| --- | --- |
| Sodium DL-2-pyrrolidone-5-carboxylate (50% aqueous soln.) | 0.10 |
| Glycerin | 0.10 |
| Protein | 0.10 |
| Dynol SAM | 42.000 |
| Ninol 2012 | 1.000 |
| Lauryl dimethylamine oxide | 2.000 |
| Deriphat 160C | 0.100 |
| Water | to 100 percent |
| Methyl Parasept | 0.150 |
| Versene Flakes | 0.100 |
| Citric acid | 0.190 |
| Monomethylol dimethyl hydantoin | 0.100 |
| Perfume | 0.300 |
| Coloring agent | 0.015 |
| Ammonium chloride | 0.600 |

EXAMPLE 3

MOISTURE STABILIZING CONDITIONER

A moisture stabilizing conditioner is formulated using the following ingredients:

| Ingredient | Weight Percent |
| --- | --- |
| Sodium DL-2-pyrrolidone-5-carboxylate (50% aqueous soln.) | 0.25 |
| Glycerin | 0.10 |
| Protein | 0.20 |
| Ethoquad 0/12 | 2.50 |
| Carbowax 4000 | 1.50 |
| Stearic acid | 1.50 |
| Glycerol monostearate | 1.50 |
| Cetyl alcohol | 2.50 |
| DL-pantothenyl alcohol | 0.10 |
| Anti-foam agent | 0.20 |
| Preservative | 0.10 |
| Coloring agent | 0.30 |
| Water | to 100 |

EXAMPLE 4

MOISTURE CONTROL SETTING CONDITIONER

A moisture control setting conditioner composition is formulated using the following ingredients:

| Ingredient | Weight Percent |
| --- | --- |
| Sodium DL-2-pyrrolidone-5-carboxylate (50% aqueous soln.) | 0.500 |
| Glycerin | 1.000 |
| Protein | 1.000 |
| GAF Quat 734 (50% of soln.) | 5.000 |
| Adogen 432 CG | 0.125 |
| Ethoquad 0/12 | 0.375 |
| SD Alcohol | 30.000 |
| Tween 20 | 0.500 |
| Water | to 100 |

The setting conditioner can additionally comprise perfuming agents, coloring agents and the like.

EXAMPLE 5

THERMAL STYLING PROTECTIVE LOTION

A blow-dry conditioning and protective lotion composition is formulated with the following ingredients:

| Ingredient | Weight Percent |
| --- | --- |
| Sodium-DL-2-pyrrolidone-5-carboxylate | 0.10 |
| Glycerin | 0.10 |
| Lexein X250 | 1.00 |
| PVP 30 | 1.00 |
| Oleyl dimethylbenzyl ammonium chloride | 0.50 |
| Water | to 100.0 |

The blow-dry composition can additionally include perfuming agents, preservatives and the like.

EXAMPLE 6

SUPPLEMENTAL GEL CONDITIONER

A supplemental gel conditioner which is used to help to restore moisture to moisture deficient hair is formulated using the following ingredients:

| Ingredient | Weight Percent |
| --- | --- |
| Sodium-DL-2-pyrrolidone-5-carboxylate (50% aqueous soln.) | 2.00 |
| Glycerin | 1.50 |
| Lexein X250 (protein) | 0.50 |
| Carbopol 940 | 0.35 |
| SD Alcohol 40 | 25.00 |
| Non-ionic surfactant | 0.5 |
| Perfuming agent | 0.1 |
| Water | to 100.0 |

EXAMPLE 7

DEEP HEAT TREATMENT CONDITIONER

A deep heat treatment conditioner which is used to help restore moisture to moderate to severe moisture deficient hair is formulated using the following ingredients.

| Ingredient | Weight Percent |
| --- | --- |
| Sodium-DL-2-pyrrolidone-5-carboxylate (50% aqueous soln.) | 5.0 |
| Glycerin | 5.0 |
| Protein | 2.5 |
| Barquat CT-429 | 4.3 |
| DL-pantothenyl alcohol | 0.1 |
| Acid stabilized glycerol monostearate | 1.0 |
| Promulgen D | 1.0 |
| Mineral oil 65/75 | 2.0 |
| Isopropyl myristate | 2.0 |
| Cetyl alcohol | 3.5 |
| Ethylene glycol monostearate | 2.0 |
| Perfume | 0.4 |
| Coloring | 0.2 |
| Water | to 100.0 |

The deep heat treatment composition is used every week on hair which is severely moisture deficient.

EXAMPLE 8

INTENSIVE CONDITIONER FOR DAMAGED HAIR

An intensive conditioner composition is formulated using the following ingredients:

| Ingredient | Weight Percent |
| --- | --- |
| Sodium-DL-2-pyrrolidone-5-carboxylate (50% aqueous soln.) | 4.00 |
| Glycerin | 3.00 |
| Protein | 4.00 |
| Barquat CT-429 | 4.3 |
| Acid stabilized glycerol monostearate | 1.0 |
| Promulgen D | 1.0 |
| Mineral oil 65/75 | 2.0 |
| Isopropyl myristate | 2.0 |
| Cetyl alcohol | 3.5 |
| Ethylene glycol monostearate | 2.0 |
| Perfume | 0.4 |
| Preservative | 0.2 |
| Water | to 100 |

EXAMPLE 9

MOISTURE CONTROL HAIR SPRAY COMPOSITION

A moisture control hair spray composition is formulated from the following ingredients:

| Ingredients | Weight Percent |
| --- | --- |
| Sodium-DL-2-pyrrolidone-5-carboxylate (50% aqueous soln.) | 0.1 |
| Glycerin | 0.1 |
| Alcohol soluble protein | 0.1 |
| PVP/VA-E-635(50%) | 10.0 |
| Silicone Fluid SF-1066 | 0.2 |
| Citric acid | 0.3 |
| Perfume | 0.3 |
| SDA 40 Alcohol | 78.6 |
| Water | to 100.0 |

It is to be understood that the foregoing examples are intended to be merely illustrative and that modifications and variations will be apparent to those skilled in the art.

I claim:

1. A method for restoring normal moisture level to severely moisture deficient hair comprising the steps of:
   (1) shampooing the hair with a moisture stabilizing shampoo;
   (2) at least once a week applying a moisture gain intensive conditioner for at least 25 minutes to said freshly shampooed hair;
   (3) at least once a week, applying a moisture gain deep heat treatment to said freshly shampooed hair;
   (4) conditioning the shampooed hair with a moisture stabilizing composition when said deep heat treatment or said moisture gain intensive treatment is not used; and
   (5) thereafter applying a moisture control styling lotion; each of said shampoos, conditioners and lotions comprising from about 0.01 to about 1.0 weight percent of sodium-2-pyrrolidone-5-carboxylate, from about 0.01 to about 5.0 weight percent of glycerin and from about 0.01 to about 5.0 weight percent of protein derived from a collagenous source.

2. The method of claim 1 additionally comprising the step of applying a moisture stabilizing night supplement to said hair at least once a week, said gel compromising from about 0.01 to about 1.0 weight percent of sodium-2-pyrrolidone-5-carboxylate, from about 0.01 to about 5.0 weight percent of glycerin and from about 0.01 to about 5.0 weight percent of protein derived from a collagenous source.

3. The method of claim 2 wherein said gel is applied to the hair twice a week.

4. The method of claim 3 wherein said gel is applied to the hair three times a week.

* * * * *